United States Patent
Hong et al.

(10) Patent No.: US 10,722,442 B2
(45) Date of Patent: Jul. 28, 2020

(54) SKIN BRIGHTENING COMPOSITION COMPRISING NOVEL GINSENOSIDE

(71) Applicant: AMOREPACIFIC CORPORATION, Seoul (KR)

(72) Inventors: Yong Deog Hong, Yongin-si (KR); Hyun Woo Jeong, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/656,082

(22) Filed: Oct. 17, 2019

(65) Prior Publication Data
US 2020/0121580 A1    Apr. 23, 2020

(30) Foreign Application Priority Data
Oct. 17, 2018  (KR) .......................... 10-2018-0123762

(51) Int. Cl.
*A61K 8/63*   (2006.01)
*A61Q 19/02*   (2006.01)

(52) U.S. Cl.
CPC ................ *A61K 8/63* (2013.01); *A61Q 19/02* (2013.01)

(58) Field of Classification Search
None
See application file for complete search history.

(56) References Cited

U.S. PATENT DOCUMENTS 8,647,610 B2 *  2/2014  Park .......................... A61K 8/60
                                                                    424/62

FOREIGN PATENT DOCUMENTS

| CN | 102875628 A | 1/2013 |
| CN | 102924556 A | 2/2013 |
| KR | 10-0178867 B1 | 3/1999 |
| KR | 10-1312389 B1 | 9/2013 |
| KR | 10-1568658 B1 | 11/2015 |
| KR | 10-2016-0086149 A | 7/2016 |
| WO | 2005/000245 A2 | 1/2005 |
| WO | 2005/000248 A1 | 1/2005 |
| WO | 2005/040189 A1 | 5/2005 |

OTHER PUBLICATIONS

Yang et al., Chemical Research in Chinese Universities (2016), 32(1), pp. 35-40.*
CAS RN: 2170771-84-1, provided by STN International Database (http://www.cas.org/training/stn/database-specific), entered into the database on Jan. 23, 2018.

* cited by examiner

*Primary Examiner* — Brian J Davis
(74) *Attorney, Agent, or Firm* — Merchant & Gould P.C.

(57) ABSTRACT

The present specification relates to a composition containing novel (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient. The composition exhibits an excellent skin brightening effect.

8 Claims, 11 Drawing Sheets

Chemical Formula: $C_{42}H_{72}O_{14}$
Exact Mass: 800.4922

1. Ginsenoside Rg1

Chemical Formula: $C_{42}H_{72}O_{13}$
Exact Mass: 784.4973

2. (20S)-Ginsenoside Rg2

Chemical Formula: $C_{48}H_{82}O_{18}$
Exact Mass: 946.5501

3. Ginsenoside Re

Chemical Formula: $C_{48}H_{82}O_{18}$
Exact Mass: 946.5501

4. Ginsenoside Rd

Chemical Formula: $C_{54}H_{92}O_{23}$
Exact Mass: 1108.6029

5. Ginsenoside Rb1

Chemical Formula: $C_{53}H_{90}O_{22}$
Exact Mass: 1078.5924

6. Ginsenoside Rb2

SKIN BRIGHTENING COMPOSITION COMPRISING NOVEL GINSENOSIDE

CROSS-REFERENCE TO RELATED APPLICATION

This application claims priority to Korean Patent Application No. 10-2018-0123762 filed on Oct. 17, 2018, and all the benefits accruing therefrom under 35 U.S.C. sctn. 119, the contents of which in its entirety are herein incorporated by reference.

BACKGROUND OF THE INVENTION

Field of the Invention

The present specification describes novel ginsenosides and compositions comprising the same.

Description of the Related Art

Ginseng (*Panax ginseng* C. A. Meyer) is a plant belonging to the genus *Panax* of the family Araliaceae. It has been used as herbal medicine from 2,000 years ago in Korea, China, Japan, etc. As the representative physiologically active ingredients of *ginseng*, saponins, polysaccharides, peptides, sitosterols, polyacetylenes and fatty acids are known, and among them, saponins of *ginseng* are called ginsenosides. The effects and efficacies of *ginseng* comprise action on the central nervous system, anticarcinogenic action, anticancer activity, immunomodulatory action, antidiabetic action, liver function improving effect, action of improving cardiovascular disorders, anti-atherosclerotic action, blood pressure controlling action, action of improving menopausal disorder, effect on osteoporosis, anti-stress action, anti-fatigue action, antioxidant action, antiaging effect, etc. The ginsenoside has a large difference in its content and composition depending on the parts such as roots, leaves, fruits, flowers, seeds, etc. of *ginseng*, but the efficacy known as above is mostly about the *ginseng* root, namely, the root part of *ginseng*, and research on other parts of *ginseng* except *ginseng* root is insufficient Melanin plays roles of protecting skin organs under the dermis by blocking ultraviolet rays in the epidermal layer and of protecting the skin by absorbing bio-free radicals. In addition, melanin is a major factor in determining the color of the skin, and when present in excess, it is also a cause of skin pigmentation such as stains, freckles, moles, or the like. Melanin is produced from melanocytes present in the basal layer of the skin, and it is known that the production is promoted by stimulation such as ultraviolet rays, inflammation, or the like. Accordingly, the production of melanin may be reduced by reducing external stimuli and blocking signal transduction, or by inhibiting the activity or synthesis of tyrosinase, which is a melanin-producing enzyme. The materials with an efficacy in inhibiting the production of melanin previously known comprise arbutin, kojic acid, or the like, but they are not highly useful due to unsatisfactory brightening effects, low stability, and skin irritation. Thus, it is necessary to develop a material that has a high brightening effect while having fewer side effects.

CITATION LIST

Patent Literature

Patent Literature 1: Korean Patent Application Publication No. 10-2016-0086149

SUMMARY OF THE INVENTION

In one aspect, the technical problem of the present invention is to provide a composition comprising a novel ginsenoside having excellent skin brightening efficacy.

In one aspect, the present disclosure provides a skin brightening composition comprising (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof as an active ingredient.

In one aspect, the present disclosure may provide a composition comprising a novel ginsenoside, a pharmaceutically acceptable salt thereof, a hydrate or solvate thereof having an excellent effect on skin brightening. The novel ginsenoside exhibits remarkably excellent skin brightening efficacy as compared to the ginsenosides previously known to have a brightening effect.

DETAILED DESCRIPTION OF THE PREFERRED EMBODIMENTS

Figure 1:
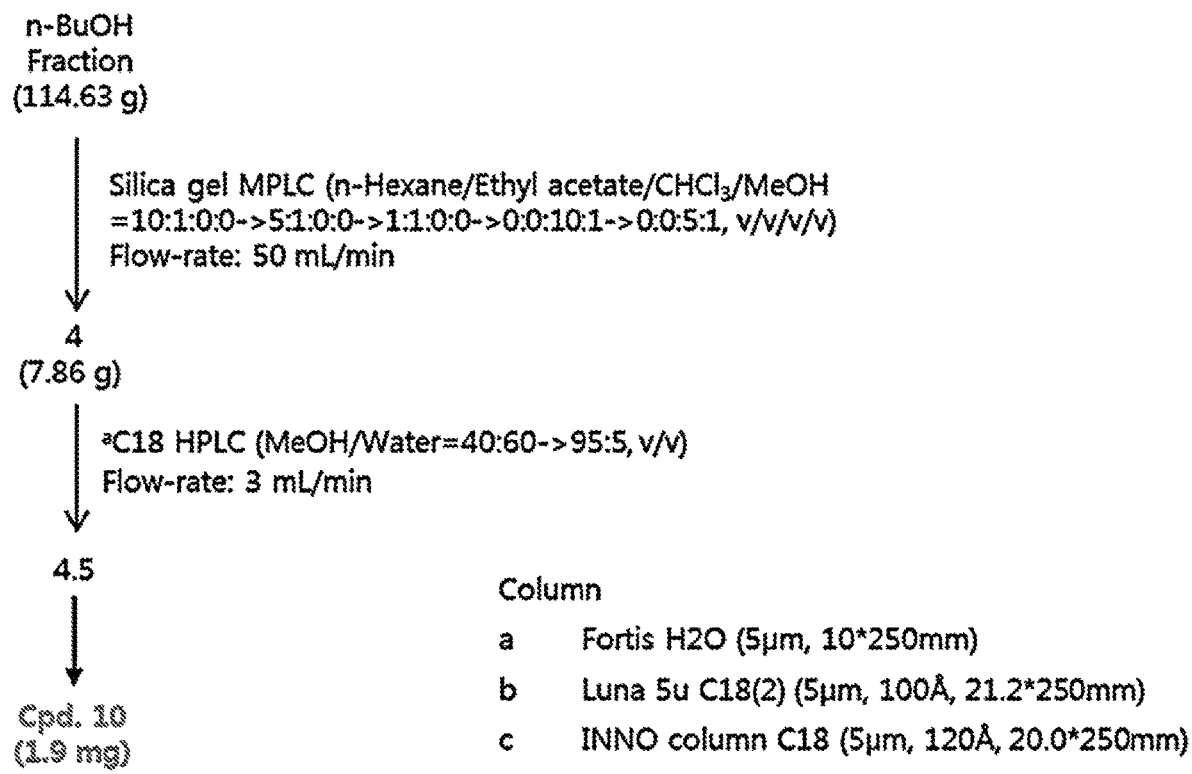
FIG. 1 is a diagram illustrating an isolation process of a novel ginsenoside (Cpd. 10) of the present disclosure among the compounds fractionated from *ginseng* seed extract.

Hereinafter, embodiments of the present disclosure will be described in more detail with reference to the accompanying drawings. However, the technology described in the present disclosure is not limited to the embodiments described herein and may be embodied in other forms. It is to be understood that the embodiments introduced herein are provided so that the disclosure can be made thorough and complete, and that the spirit of the present disclosure can be fully conveyed to those skilled in the art. In order to clearly express each constituent in the drawings, the size, such as the width or thickness, etc. of the constituent, is shown to be somewhat enlarged. In addition, although only a part of the constituents are shown for convenience of explanation, those skilled in the art will be able to easily understand the rest parts of the constituents. In addition, those having ordinary skill in the pertinent field may implement the spirit of the present disclosure in various other forms without departing from the technical spirit of the present disclosure.

In one embodiment, the present disclosure may provide a skin brightening composition comprising a novel ginsenoside, a pharmaceutically acceptable salt thereof, a hydrate or a solvate thereof as an active ingredient.

In one embodiment, the ginsenoside is a novel triterpene saponin, and is (20S,24R)-6-O-β-D-glucopyranosyl(1→2)-β-D-glucopyranoside-dammar-3-one-20,24-epoxy-6a,12b,25-triol.

One embodiment may provide a use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof for use in the preparation of a composition for skin brightening.

One embodiment may provide a method of skin brightening comprising administering (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof in an effective amount to a subject in need thereof. In one embodiment, the method may comprise administering to a subject with pigmentation site or dark skin tones.

One embodiment may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for use in a composition for skin brightening. In addition, a non-therapeutic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof, or a solvate thereof as an active ingredient for skin brightening may be provided.

As used herein, the term "pharmaceutically acceptable" refers to those that can be approved or was approved by the government or equivalent regulatory agencies for use in animals, more specifically in humans, by avoiding significant toxic effects when used in conventional medicinal dosage, or those recognized as being listed in the pharmacopoeia or described in other general pharmacopoeia.

As used herein, the term "pharmaceutically acceptable salt" refers to a salt according to one aspect of the present disclosure that is pharmaceutically acceptable and possesses the desired pharmacological activity of the parent compound. The salts comprise (1) acid addition salts, formed with inorganic acids such as hydrochloric acid, hydrobromic acid, sulfuric acid, nitric acid, phosphoric acid, or the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, or the like; or (2) salts formed when an acidic proton present in the parent compound is substituted.

As used herein, the term "hydrate" refers to a compound to which water is bound, and is a broad concept comprising an inclusion compound having no chemical bonding force between water and the compound.

As used herein, the term "solvate" refers to a compound of higher order produced between molecules or ions of a solute and molecules or ions of a solvent.

In one embodiment, the molecular formula of ginsenoside is $C_{42}H_7O_{15}$, and has the following chemical structure.

[Formula 1]

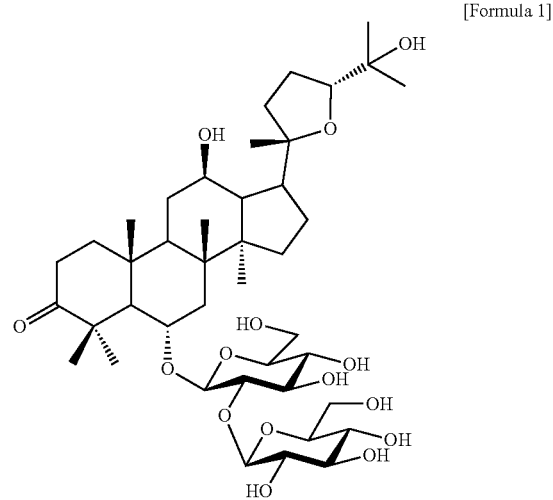

In the present specification, the novel ginsenosides are named "pseudoginsenoside $RT_8$," or "PG-$RT_8$."

In one embodiment, the ginsenoside may be isolated from the *ginseng* seed extract, but is not limited thereto. In one embodiment, the *ginseng* of the *ginseng* seed is *Panax ginseng* C.A. Meyer.

As used herein, the term "isolation" is meant to comprise those extracted or fractionated from *ginseng* seed extract, and may use water, organic solvents, or the like, and any method known to those skilled in the art may also be applied. The fraction may be performed after the extraction.

As used herein, the term "extract" means a substance obtained by extracting a component contained inside of a natural substance, regardless of the extracted method or ingredients.

The term is used in a broad sense comprising, for example, all of those obtained by extracting a component soluble in a solvent from a natural substance using water or an organic solvent, extracting only a specific component of a natural substance, or the like.

As used herein, "fractions" comprise those obtained by fractionating a specific substance or extract using a certain solvent or those leftover after fractions, and extracting them again with a specific solvent. Fractional methods and extraction methods may be any method known to those skilled in the art.

As used herein, the term "prevention" refers to any action that inhibits or delays a desired symptom by administering a composition according to one embodiment of the present disclosure. As used herein, the term "treatment" refers to any action that improves or disappears a desired symptom or disease by administering a composition according to one embodiment of the present disclosure. As used herein, the term "improvement" refers to any action in which a desired symptom is improved or advantageously changed from before administration by administering a composition according to one embodiment of the present disclosure.

In one embodiment, the ginsenoside may be isolated from ginseng seed methanol- and butanol-soluble extract. Specifically, the ginsenoside may be detected and isolated by analyzing methanol- and butanol-soluble extracts of ginseng seed using HPLC-ESI-Q-TOF-MS. Not all triterpenes and steroidal saponins can be observed by HPLC-UV or HPLC-ELSD from ginseng seed crude extract because the main component of ginseng seed extract is lipid.

In one embodiment, the present disclosure may provide a composition for inhibiting the production of melanin by comprising the ginsenoside, a pharmaceutically acceptable salt thereof, a hydrate thereof, or a solvate thereof. In one embodiment, the present disclosure may provide a composition for inhibiting the tyrosinase activity by comprising the ginsenoside, a pharmaceutically acceptable salt thereof, a hydrate thereof, or a solvate thereof.

In one embodiment, the present disclosure may provide a composition having a remarkably excellent skin brightening efficacy as compared to conventional ginsenosides known to have skin brightening efficacy.

In one embodiment, the present disclosure may contain the active ingredient in an amount of 0.0001 to 99.9% by weight based on the total weight of the composition. Specifically, as one embodiment, the composition may contain the active ingredient in an amount of at least 0.0001% by weight, at least 0.0005% by weight, at least 0.001% by weight, at least 0.01% by weight, at least 0.1% by weight, at least 1% by weight, at least 2% by weight, at least 3% by weight, at least 4% by weight, at least 5% by weight, at least 6% by weight, at least 7% by weight, at least 8% by weight, at least 9% by weight, at least 10% by weight, at least 15% by weight, at least 20% by weight, at least 25% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, at least 85% by weight, at least 90% by weight, at least 95% by weight, or at least 99.9% by weight based on the total weight of the composition, but is not limited to the above range. In addition, as one embodiment, the composition may contain the active ingredient in an amount of 100% or less by weight, 99% or less by weight, 95% or less by weight, 90% or less by weight, 85% or less by weight, 80% or less by weight, 75% or less by weight, 70% or less by weight, 65% or less by weight, 60% or less by weight, 55% or less by weight, 50% or less by weight, 45% or less by weight, 40% or less by weight, 35% or less by weight, 30% or less by weight, 25% or less by weight, 20% or less by weight, 15% or less by weight, 10% or less by weight, 9% or less by weight, 8% or less by weight, 7% or less by weight, 6% or less by weight, 5% or less by weight, 4% or less by weight, 3% or less by weight, 2% or less by weight, 1% or less by weight, 0.5% or less by weight, 0.1% or less by weight, 0.01% or less by weight, 0.001% or less by weight or 0.0005% or less by weight based on the total weight of the composition, but is not limited to the above range.

In one embodiment, the dosage may be 0.05 mg/kg/day to 10 g/kg/day. In one embodiment, the dosage of the composition may vary depending on the judgement such as age, sex, and weight of the subject, the specific disease or pathology of the subject, the severity of the disease or pathologic state, the route of administration, or the like. The determination of dosage based on these factors is within the level of those skilled in the art. For example, the dosage may be at least 0.05 mg/kg/day or at least 1 mg/kg/day, and may be at most 10 g/kg/day, at most 100 mg/kg/day or at most 10 mg/kg/day. However, the dosage does not limit the scope of the present specification in any way.

The composition according to embodiments of the present disclosure may be a composition for external skin application comprising the active ingredients.

As used herein, "skin" means the tissue covering the body surface of an animal and is used in the broadest sense, comprising not only the tissue that covers the face or body but also the scalp and hair.

The composition according to the embodiments of the present disclosure may be a cosmetic composition comprising the active ingredients.

In one embodiment, the composition may be formulated by comprising a cosmetologically or dermatologically allowable medium or base. It may be provided in any topically applicable form comprising, for example, solutions, gels, anhydrous solids or pastes, oil-in-water emulsions, suspensions, microemulsions, microcapsules, microgranules, ionic (liposomes) or non-ionic vesicular dispersions, creams, skin lotions, milk lotions, powders, ointments, sprays and concealing sticks. In addition, the composition may also be used in the form of foam or an aerosol composition further containing compressed propellants. Such compositions may be prepared by a method commonly employed in the pertinent field.

The composition according to the embodiments of the present disclosure may be a food composition comprising the active ingredients.

For example, it may be processed into functional foods such as fermented milk, cheese, yogurt, juice, probiotic and health food containing the active ingredient, and may be used in the form of various other food additives. In one embodiment, the composition may be a composition for health food. In one embodiment, the composition for health food may be formulated into pills, capsules, tablets, granules, caramels, drinks, or the like. In another embodiment, the composition may be processed in the form of liquid, powder, granules, tablets, tea bags, or the like. The composition may be administered by various methods such as simple drinking, injection administration, spray administration or squeeze administration, or the like. The composition may contain other components that can give a synergistic effect to the main effect within a range that does not impair the main effect of the present disclosure. For example, it may further comprise additives such as perfumes, pigments, fungicides, antioxidants, preservatives, moisturizers, thickeners, inorganic salts, emulsifiers and synthetic polymer materials, or the like for improving the physical properties. In addition, the composition may further comprise auxiliary components, comprising water-soluble vitamins, oil-soluble vitamins, polymer peptides, polysaccharides and seaweed extracts. The above components may be suitably selected and mixed by those skilled in the art depending on the formulation or purpose of use and may be added in an amount selected within the range that does not impair the object and effect of the present disclosure. For example, the above components may be added in an amount of 0.0001 to 99.9% by weight based on the total weight of the composition.

The composition according to the embodiments of the present disclosure may be a pharmaceutical composition comprising the active ingredients. The pharmaceutical composition may further comprise a pharmaceutical adjuvant such as antiseptic, stabilizer, hydrating agent, emulsifying accelerator, salt and/or buffer for controlling osmotic pressure, etc. or other therapeutically useful substance.

In one embodiment, the pharmaceutical composition may be a formulation for oral administration. The formulation for oral administration may comprise, for example, tablet, pill, hard or soft capsule, liquid, suspension, emulsion, syrup, powder, dust, granule, pellet, or the like. These formulations may comprise, in addition to the active ingredient, a surfactant, a diluent (e.g., lactose, dextrose, sucrose, mannitol, sorbitol, cellulose or glycine) or a lubricant (e.g., silica, talc, stearic acid and magnesium or calcium salt thereof, or polyethylene glycol). The tablet may comprise a binder such as magnesium aluminum silicate, starch paste, gelatin, tragacanth, methyl cellulose, sodium carboxymethyl cellulose and polyvinylpyrrolidone, and may occasionally comprise a pharmaceutical additive such as a disintegrant, e.g. starch, agar, alginic acid or a sodium salt thereof, an absorbent, a colorant, a flavor, a sweetener, or the like. The tablet may be prepared according to the commonly employed mixing, granulation or coating method.

In one embodiment, the pharmaceutical composition may be a formulation for parenteral administration, and the formulation for parenteral administration may be rectal, topical, subcutaneous, transdermal dosage form. The formulation for parenteral administration may comprise, for example, injection, drop, ointment, lotion, gel, cream, spray, suspension, emulsion, suppository, patch, etc., but is not limited thereto.

In one embodiment, the dose of the pharmaceutical composition may be varied with the age, sex and body weight of a subject to be treated, particular disease or pathological condition be treated, severity of the disease or pathological condition, administration route and the judgment of a prescriber. Determination of the dose considering these factors is within the level of those skilled in the art. For example, the dosage may be at least 0.05 mg/kg/day or at least 1 mg/kg/day, and may be at most 10 g/kg/day, at most 100 mg/kg/day or at most 10 mg/kg/day. However, the dosage does not limit the scope of the present specification in any way.

Hereinafter, the present disclosure will be described in detail with reference to examples, comparative examples and test examples. These are only presented by way of example only to more specifically describe the present disclosure, and it is obvious to those skilled in the art that the scope of the present disclosure is not limited by these examples, comparative examples and test examples.

All experimental values below represent the average of values obtained by repeating experiments three or more times, and standard deviation (SD) is indicated by error bars. p values were calculated by one-way ANOVA and Dunnett test, and p values less than 0.05 were considered statistically significant.

[Example 1] Isolation of Ginsenosides

Fraction 5.5 kg of ginseng seed (seeds of Panax ginseng) was finely ground in a mixer to make a powder form, extracted with methanol, and then fractionated step by step using n-hexane, ethyl acetate, n-butanol, and the like. Lipids were mostly removed by n-hexane, and the lipids remaining in the ethyl acetate fraction were suspended in methanol:water=1:1 (v/v), stored in the freezer overnight, and then only the supernatant was taken. The lipids were removed once more using a centrifuge. 2.61 g of ethyl acetate fraction and 114.64 g of n-butanol fraction thus pretreated were fractionated through column and HPCCC (High Performance Counter-Current Chromatography) as follows.

Fraction Using Columns of n-Butanol Fractions and HPCCC 114.64 g of n-butanol fraction was fractionated by MPLC, and the solvent used then was n-hexane/ethyl acetate=10:1→5:1→1:1→CHCl$_3$/MeOH=10:1→5:1 (v/v) and flow rate was 50 mL/min. The above conditions were used to make a total of 12 subfractions, and the components contained in each fraction were separated again using HPCCC, HPLC (High-performance liquid chromatography), Sephadex LH-20 column, or the like. 16 compounds were investigated by identifying their structure using NMR (Nuclear magnetic resonance), UV (Ultraviolet rays), and MS (Mass spectrometry).

The 16 compounds isolated comprise ginsenoside Rg1 (compound 1), ginsenoside Rg2 (compound 2) and ginsenoside Re (compound 3), which are protopanaxatriol saponins; ginsenoside Rd (compound 4), ginsenoside Rb1 (compound 5) and ginsenoside Rb2 (compound 6), which are protopanaxadiol saponins; stigma-5-en-3-O-β-D-glucopyranoside (compound 7), stigma-5,24(28)-dien-3-O-β-D-glucopyranoside (compound 8) and stigma-5,22-dien-3-O-β-D-glucopyranoside (compound 9), which are sterol glycosides; (20S,24R)-6-O-β-D-glucopyranosyl(1→2)-β-D-glucopyranoside-dammar-3-one-20,24-epoxy-6a,12b,25-triol (compound 10), a novel compound that is first isolated from nature as a novel ginsenoside according to an embodiment of the present disclosure; phenethyl alcohol β-D-xylopyranosyl(1→6)-β-D-glucopyranoside (compound 12) and Eugenyl R-gentiobioside (compound 13), which are phenolic glycosides; isorhamnetin 3-O-β-D-glucopyranoside (compound 15), which is flavonoid; and adenosine (compound 11), uracil (compound 14) and tryptophan (compound 16), which are primary metabolites.

Figure 2:
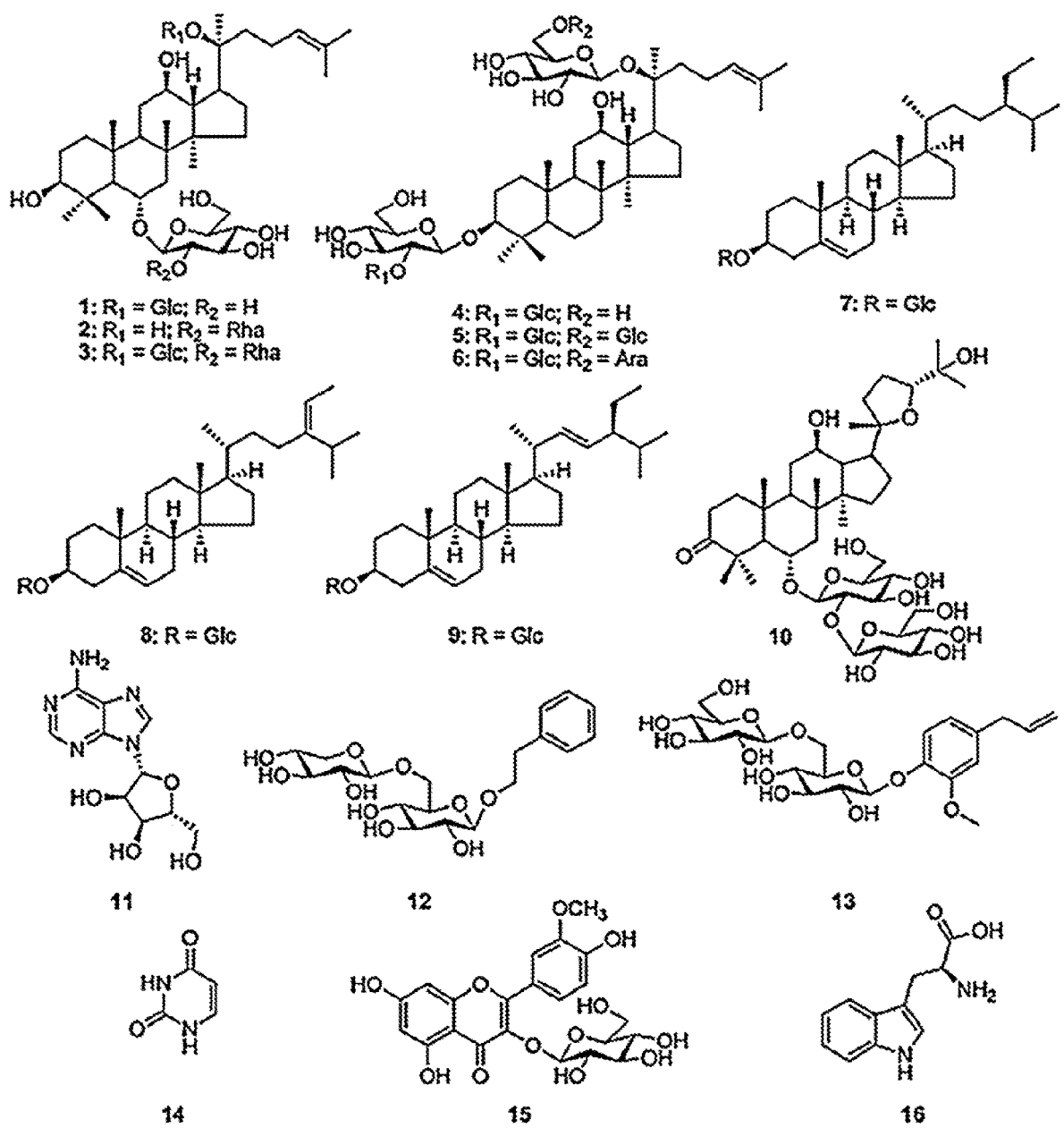
FIG. 2 is a diagram illustrating the chemical structures of 16 compounds fractionated from *ginseng* seed extract.
Figure 3:
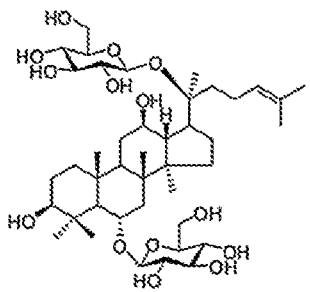
FIG. 3 is a diagram illustrating the spectroscopic evidence and structures of compounds 1 to 6 corresponding to the previously known ginsenosides among the compounds fractionated from *ginseng* seed extract.
Figure 3:
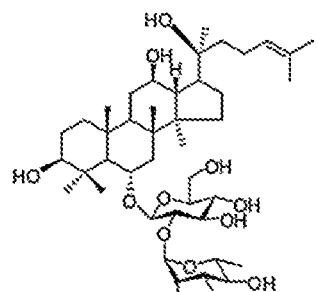
Figure 3:
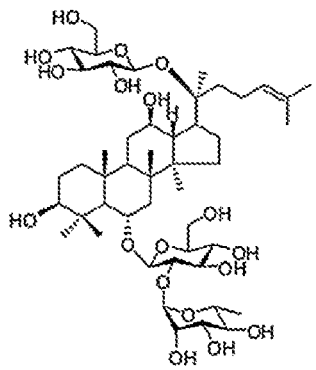
Figure 3:
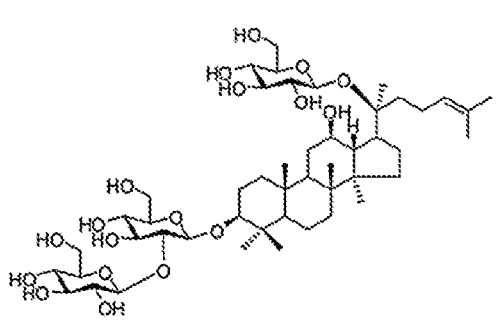
Figure 3:
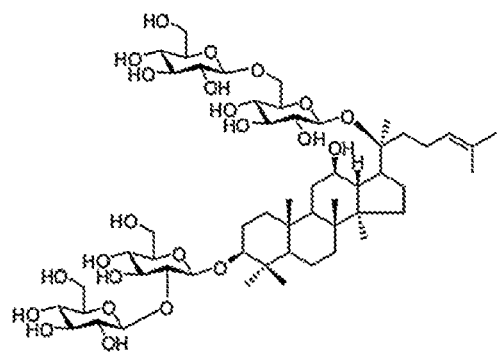
Figure 3:
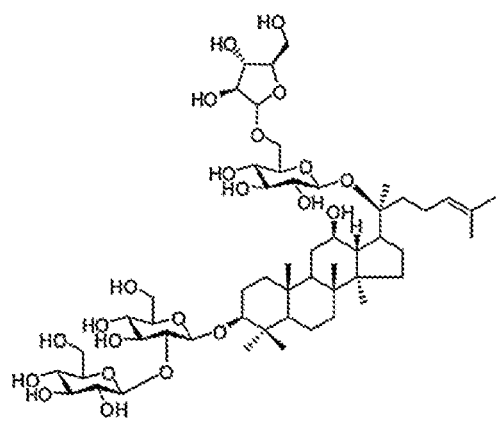
Figure 4:
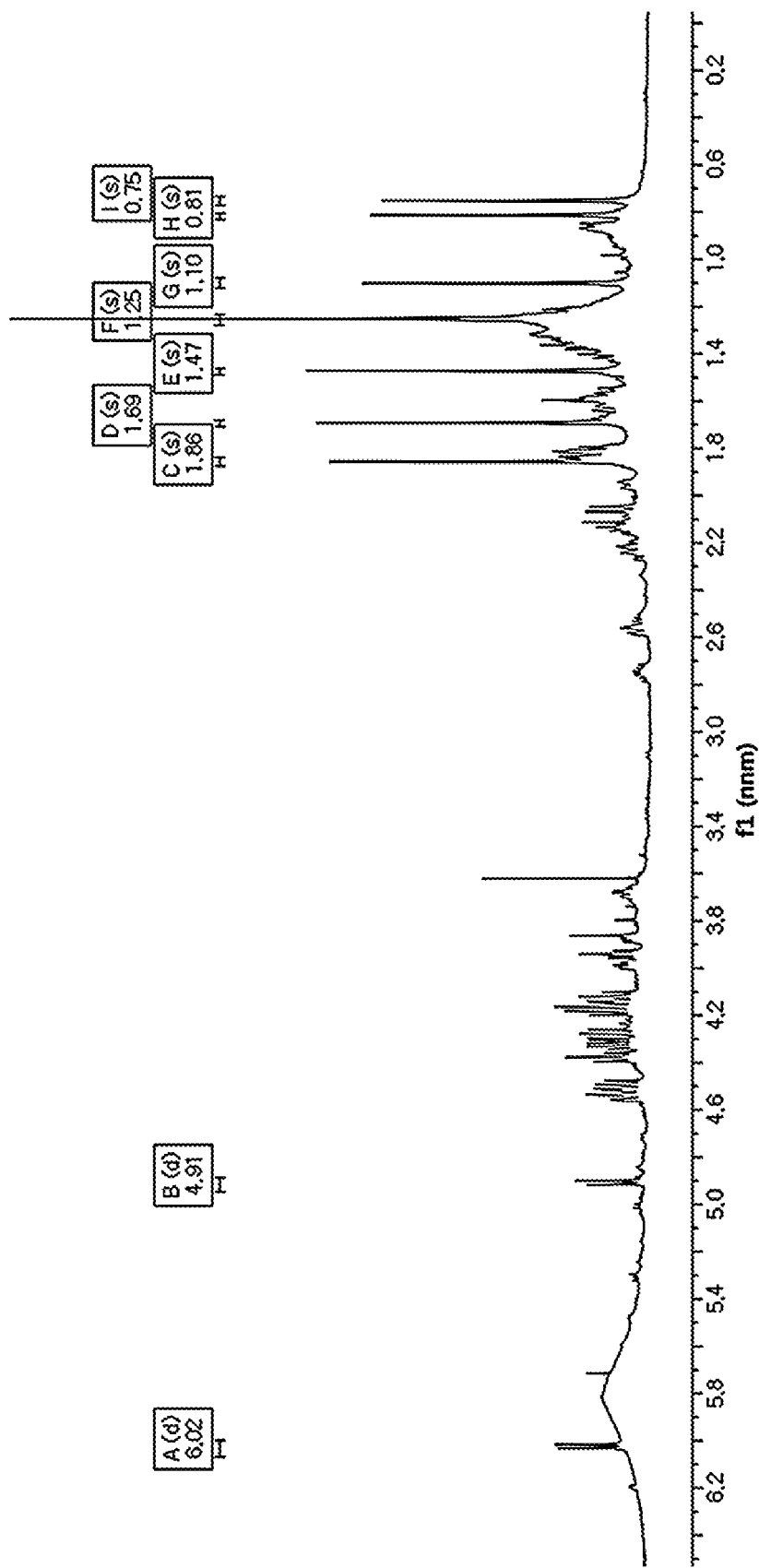
FIG. 4 is a diagram illustrating a 1H-NMR spectrum of compound 10 corresponding to the novel ginsenoside of the present disclosure among the compounds fractionated from *ginseng* seed extract.
Figure 5:
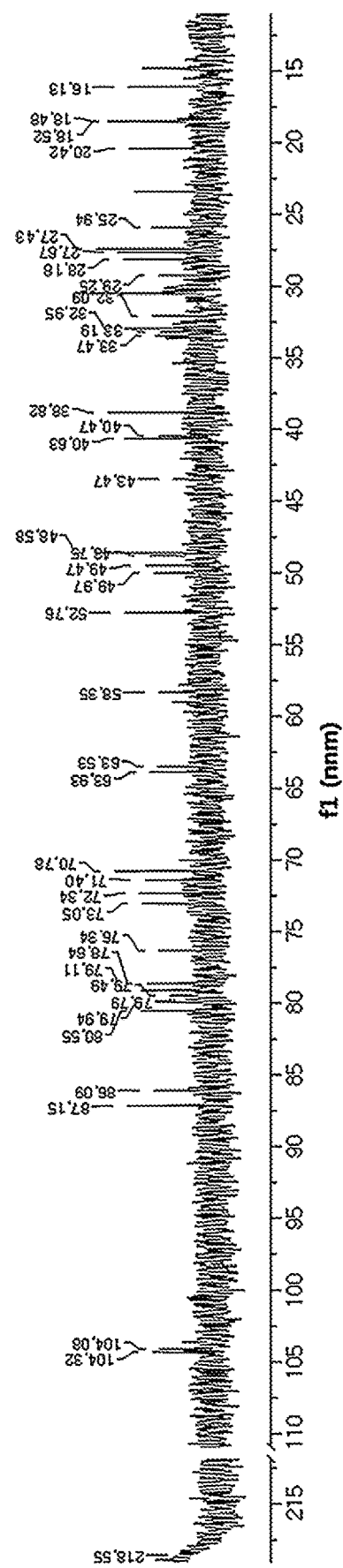
FIG. 5 is a diagram illustrating a $^{13}$C-NMR spectrum of compound 10 corresponding to the novel ginsenoside of the present disclosure among the compounds fractionated from *ginseng* seed extract.
Figure 6:
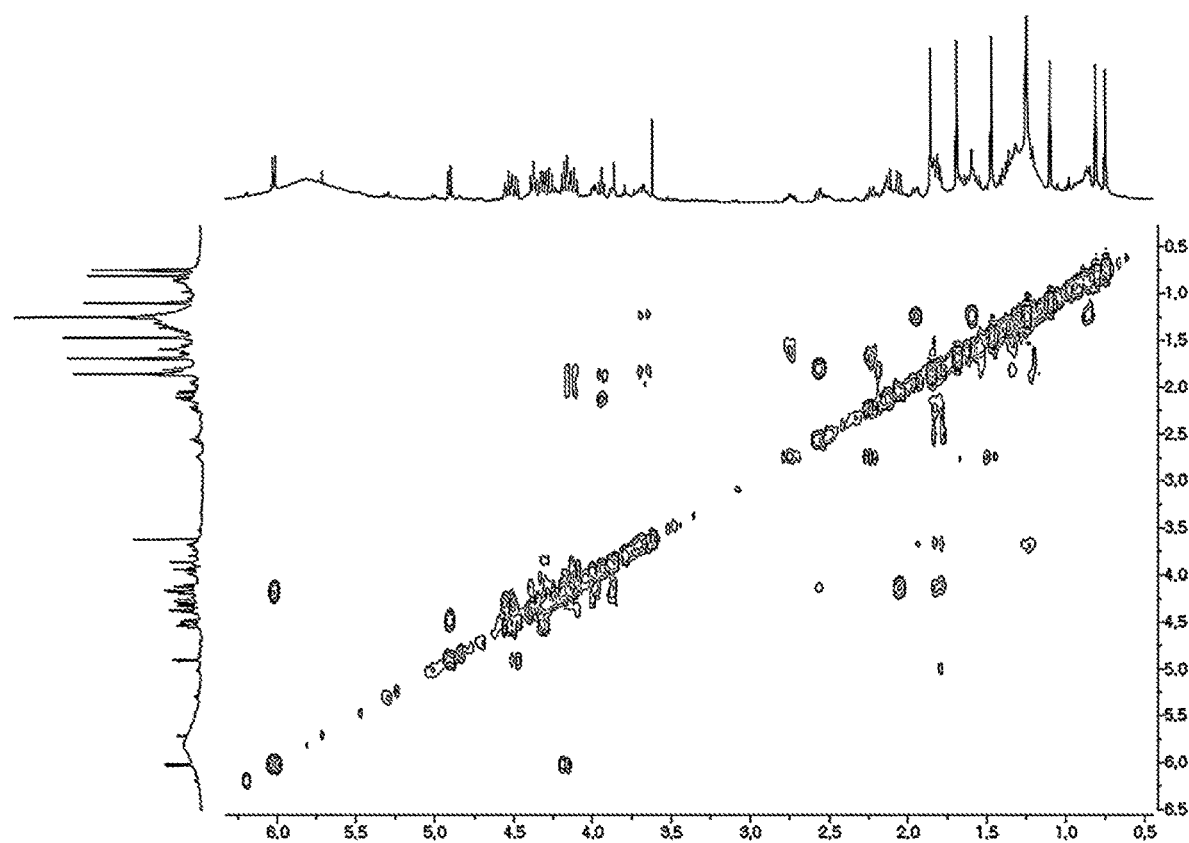
FIG. 6 is a diagram illustrating a COSY spectrum of compound 10 corresponding to the novel ginsenoside of the present disclosure among the compounds fractionated from *ginseng* seed extract.
Figure 7:
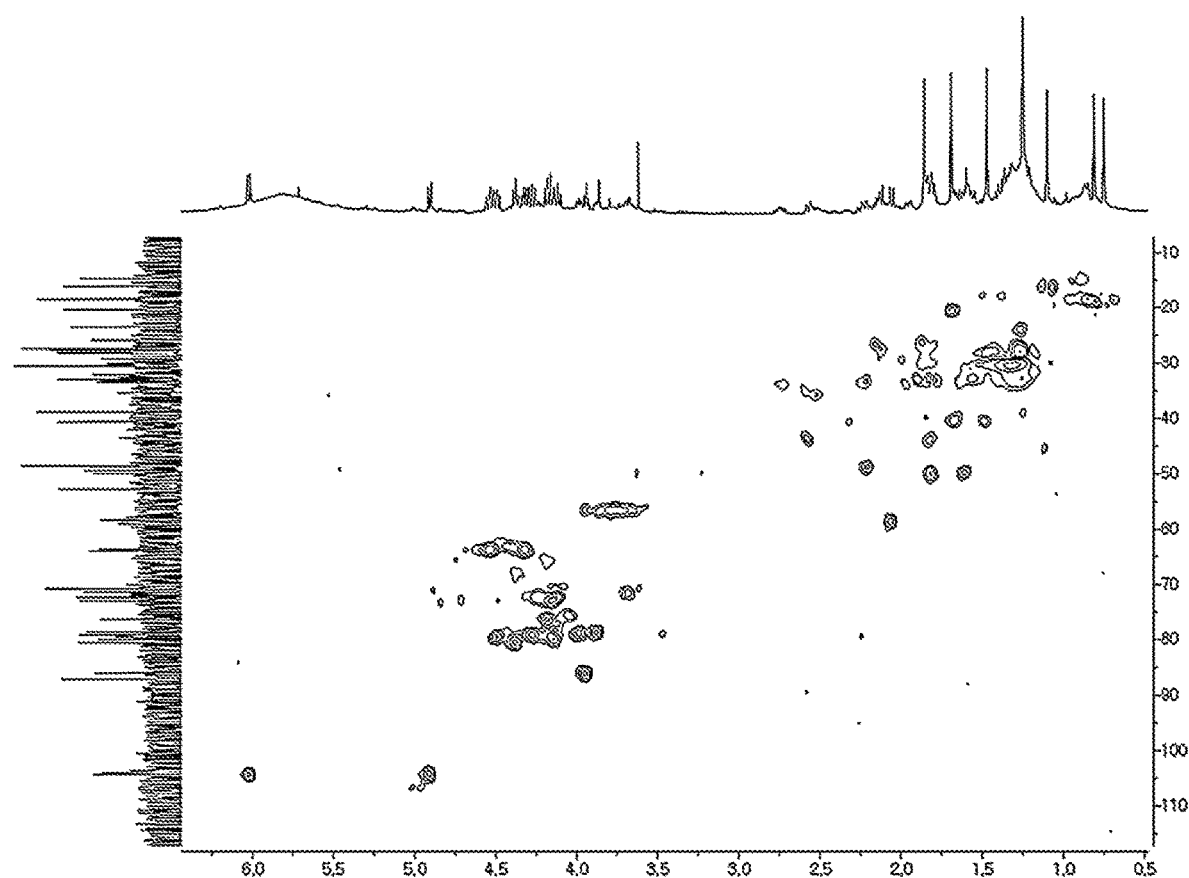
FIG. 7 is a diagram illustrating an HSQC spectrum of compound 10 corresponding to the novel ginsenoside of the present disclosure among the compounds fractionated from *ginseng* seed extract.
Figure 8:
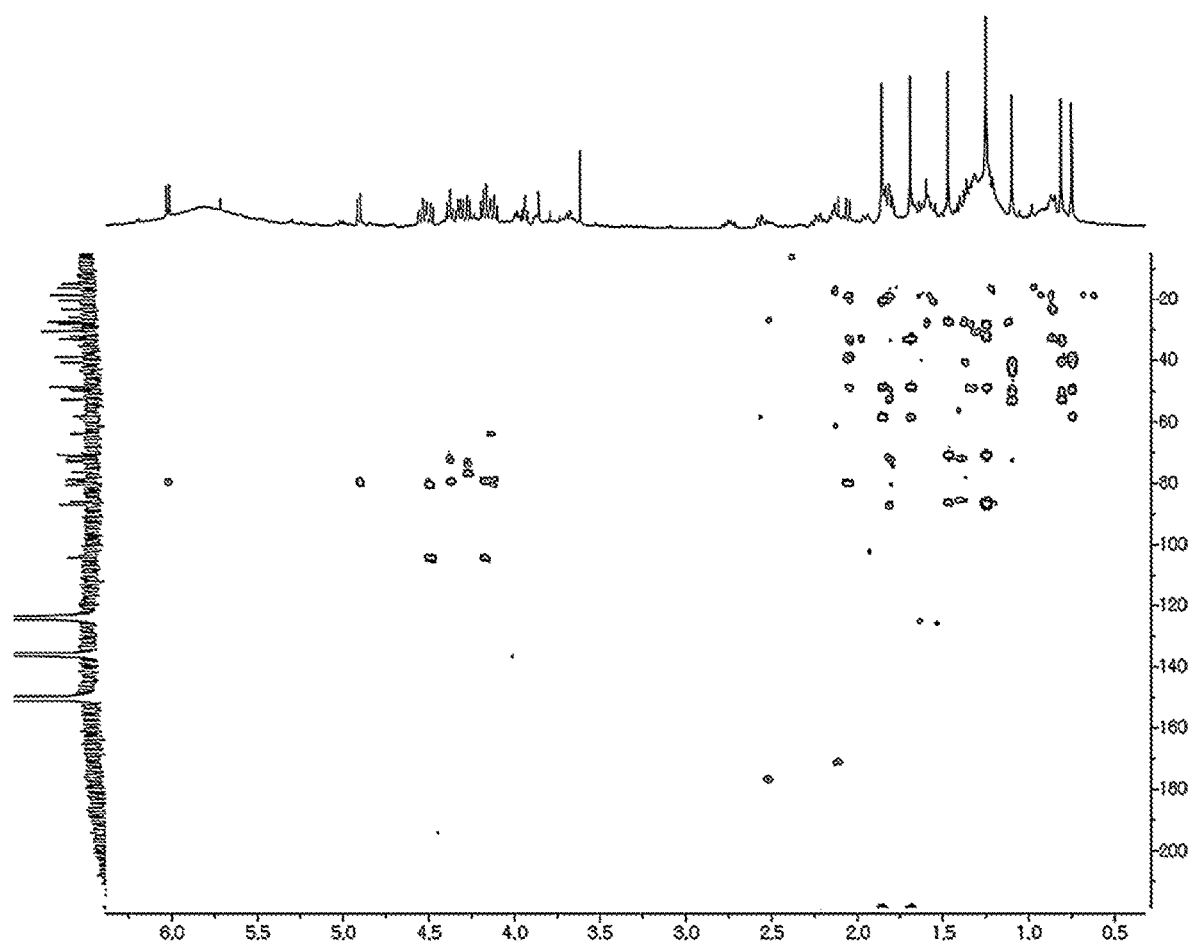
FIG. 8 is a diagram illustrating an HMBC spectrum of compound 10 corresponding to the novel ginsenoside of the present disclosure among the compounds fractionated from *ginseng* seed extract.
Figure 9:
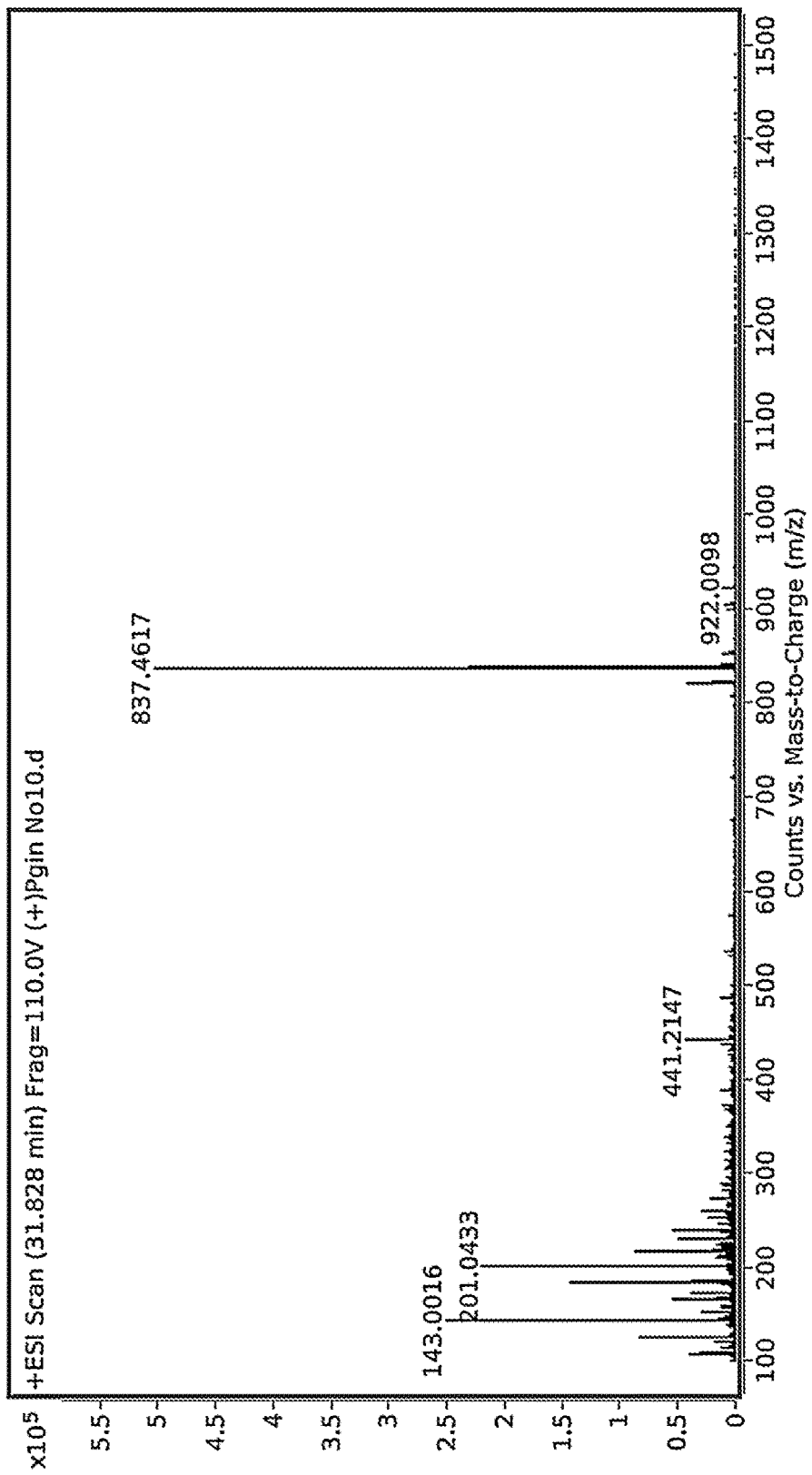
FIG. 9 is a diagram illustrating an MS spectrum of compound 10 corresponding to the novel ginsenoside of the present disclosure among the compounds fractionated from *ginseng* seed extract.
Figure 10:
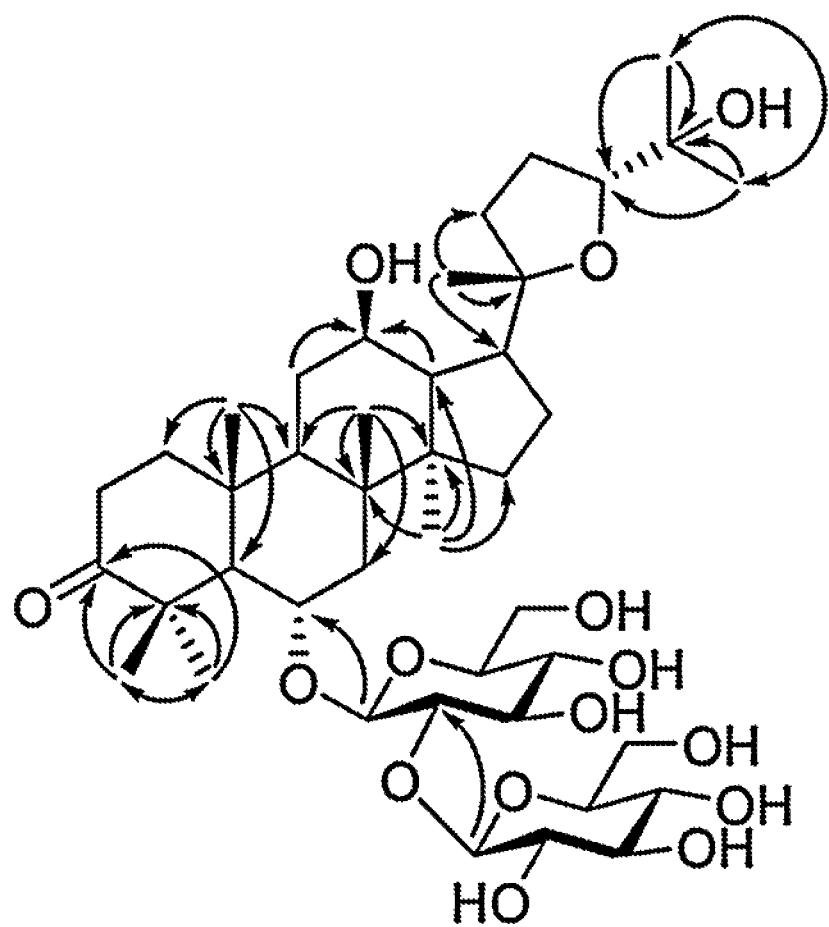
FIG. 10 is a diagram illustrating the core HMBC correlation of compound 10 corresponding to the novel ginsenoside of the present disclosure among the compounds fractionated from *ginseng* seed extract.

An isolation process of a novel ginsenoside according to an embodiment of the present disclosure corresponding to compound 10 above is shown in FIG. 1. The chemical structures of the 16 compounds are shown in FIG. 2, and spectroscopic evidence and chemical structures of the conventionally known ginsenoside compounds 1-6 among the above compounds are separately shown in FIG. 3.

Compound 10 was isolated as a white amorphous powder showing the molecular formula of $C_{42}H_{70}O_5$ based on the sodiated pseudomolecular ion peak at m/z 837.4617 [(M+Na)$^+$ calcd. 837.4612] in the cationic ESI-Q-TOF-MS (Electrospray Ionization-Quadrupole-Time-of-flight mass spectrometry) spectrum. The 1H NMR spectrum of the compound 10 contained 8 methyl resonances in [$δ_H$ 1.86 (3H, s, H-28), 1.69 (3H, s, H-29), 1.47 (3H, s, H-27), 1.25 (6H, s, H-21, 26), 1.10 (3H, s, H-18), 0.81 (3H, s, H-30), 0.75 (3H, s, H-19)]. In addition, two pairs of signals corresponding to the anomeric protons and carbon atoms at the two sugar residues were detected at $δ_H$ 6.02 (1H, d, J=7.8, H-2")/$\delta_C$ 104.08 (C-1') and $_H$4.91 (1H, d, J=7.7, H-1')/$\delta_C$ 104.32 (C-1"). $^{13}$C NMR and heteronuclear single quantum correlation (HSQC) spectra revealed 42 carbon signals. Apart from the two sugar residues above, the aglycone of compound 10 had eight methylenes, four methines, three oxygen-containing methines [$\delta_C$ 79.79 (C-6), 71.40 (C-12) and 86.09 (C-24)], five quaternary carbon atoms, two oxygenated quaternary carbon atoms [$\delta_C$ 87.15 (C-20) and 70.78 (C-25)], and eight methyl groups and carbonyl carbon [$\delta_C$ 218.85 (C-3)]. As a result of thorough interpretation of $^1$H and $^{13}$C NMR data, the aglycone of compound 10 was found to be superimposed on pseudoginsengenin R1 [(20S,24R)-dammar-3-one-20,24-epoxy-6a,12β,25-triol]). The absolute configuration of C-20 in compound 10 was deduced from S to chemical shift of C-21 ($\delta_C$ 27.67), and the 24R configuration was determined by chemical shift of C-24 ($\delta_C$ 86.09) as previously disclosed. Both sugar units were turned out to be β-D-glucopyranosyl residues from the coupling constants of the anomeric protons at $^1$H NMR spectra and 12 carbon resonances, together with acid hydrolysis data and gas chromatography (GC) analysis results. A glycoside linkage was determined by heteronuclear multiple bond correlation (HMBC) which showed cross peaks at $\delta_H$ 6.02 (H-1")/$\delta_C$ 79.49 (C-2') and $\delta_H$ 4.91 (H-1')/5c 79.79 (C-6), and it was demonstrated that 2-O-(β-D-glucopyranosyl)-β-D-glucopyranosyl residues were linked to C-6 of aglycone at pseudoginsengenin R1. Each of the analytical spectra of the compound 10 and the core HBMC correlation are shown in FIGS. 4 to 10.

In the above analysis results, it was determined that the chemical structure of compound 10 was (20S,24R)-6-O-β-D-glucopyranosyl(1→2)-β-D-glucopyranoside-dammar-3-one-20,24-epoxy-6a,12b,25-triol, and named pseudoginsenoside RT8 (PG-RT$_8$).

Among the ginsenosides isolated from the *ginseng* seed extract, ginsenoside Rg1 (compound 1), ginsenoside Rg2 (compound 2) and ginsenoside Re (compound 3), which are PPT (ProtoPanaxTriol) based ginsenosides, comprise three hydroxyl groups in the ginsenoside backbone. Ginsenoside Rd (compound 4), ginsenoside Rb1 (compound 5), and ginsenoside Rb2 (compound 6), which are PPD (ProtoPanax Diol) based ginsenosides, comprise two hydroxyl groups in the ginsenoside backbone. On the other hand, compound 10, which is a newly isolated and identified ginsenoside in the present disclosure, has a PPT-based backbone, but the terminal hydroxyl group of the backbone is ketone, and there is a structural difference in that the linear chain of ginsenoside is cyclized with a furan ring.

In the present disclosure, the molecular formula of the newly isolated and identified compound 10 was $C_{42}H_{70}O_{15}$, ESI-Q-TOF-MS, m/z was 837.4617 [M+Na]$^+$, and $^1$H, $^{13}$C-NMR spectra are shown in the following table.

TABLE 1

| Position | 13C-NMR | 1H-NMR |
|---|---|---|
| 1 | 40.63 | 1.67 (1H, H-1a)$^a$, 1.49 (1H, H-1b)$^a$ |
| 2 | 33.61 | 2.23 (1H, H-2a)$^a$, 1.78 (1H, H-2b)$^a$ |
| 3 | 218.85 | — |
| 4 | 48.58 | — |
| 5 | 58.35 | 2.06 (1H, d, J = 10.6 Hz, H-5) |
| 6 | 79.79 | 4.15 (1H-6)$^a$ |
| 7 | 43.47 | 2.57 (1H, H-7a)$^a$, 1.82 (1H, H-7b)$^a$ |
| 8 | 40.47 | — |
| 9 | 49.47 | 1.60 (1H, H-9)$^a$ |
| 10 | 38.82 | — |
| 11 | 33.47 | 2.22 (1H, H-11a)$^a$, 1.32 (1H, H-11b)$^a$ |
| 12 | 71.40 | 3.68 (1H, td, J = 10.6, 4.5 Hz, H-12) |

TABLE 1-continued

| Position | 13C-NMR | 1H-NMR |
|---|---|---|
| 13 | 49.97 | 1.81 (1H, H-13)$^a$ |
| 14 | 52.76 | — |
| 15 | 33.19 | 1.64 (1H, H-15a)$^a$, 1.26 (1H, H-15b)$^a$ |
| 16 | 25.94 | 2.17 (1H, H-16a)$^a$, 1.87 (1H, H-16b)$^a$ |
| 17 | 48.75 | 2.21 (1H, H-17)$^a$ |
| 18 | 16.13 | 1.10 (3H, s, H-18) |
| 19 | 18.48 | 0.75 (3H, s, H-19) |
| 20 | 87.15 | — |
| 21 | 27.67 | 1.25 (3H, s, H-21) |
| 22 | 32.09 | 1.60 (1H, H-22a)$^a$, 1.37 (1H, H-22b)$^a$ |
| 23 | 29.25 | 1.82 (1H, H-23a)$^a$, 1.25 (1H, H-23b)$^a$ |
| 24 | 86.09 | 3.94 (1H, t, J = 7.5 Hz, H-24) |
| 25 | 70.78 | — |
| 26 | 27.43 | 1.25 (3H, s, H-26) |
| 27 | 28.18 | 1.45 (3H, s, H-27) |
| 28 | 32.95 | 1.86 (3H, s, H-28) |
| 29 | 20.42 | 1.69 (3H, s, H-29) |
| 30 | 18.52 | 0.81 (3H, s, H-30) |

$^a$peak was overlapped

TABLE 2

| Position | 13C-NMR | 1H-NMR |
|---|---|---|
| 6-O-Glc | | |
| 1' | 104.08 | 4.91 (2H, d, J = 7.7 Hz, H-1') |
| 2' | 79.49 | 4.48 (1H, m, H-2') |
| 3' | 80.55 | 4.38 (1H, m, H-3') |
| 4' | 73.05 | 4.16 (1H, m, H-4') |
| 5' | 79.94 | 4.15 (1H, m, H-5') |
| 6' | 63.53 | 4.54 (1H, m, H-6'a), 4.32 (1H, m, H-6'b) |
| 2'-O-Glc | | |
| 1" | 104.32 | 6.02 (1H, d, J = 7.8 Hz, H-1") |
| 2" | 76.34 | 4.18 (1H, m, H-2") |
| 3" | 78.64 | 3.99 (1H, m, H-3") |
| 4" | 72.34 | 4.12 (1H, m, H-4") |
| 5" | 79.11 | 4.27 (1H, m, H-5") |
| 6" | 63.93 | 4.54 (1H, m, H-6"a), 4.32 (1H, m, H-6"b) |

[Test Example 1] Comparison of Skin Brightening Efficacy 1

In order to compare the skin brightening effects of ginsenosides isolated from the *ginseng* seed extract, the inhibitory effect of the tyrosinase activity was evaluated as follows.

Mushroom-derived tyrosinase and tyrosine were obtained from Sigma Chemical. With 150 µl of 0.1 M phosphate buffer (pH 6.5), 8 µl of mushroom tyrosinase (2,100 unit/ml) and 0.05 M concentration of L-tyrosine, the novel ginsenoside GS #10 of an embodiment of the present disclosure isolated from the *ginseng* seed extract and ginsenosides GS #01-GS #06, which are comparative examples of the present disclosure, were treated at 5 ppm, 10 ppm, 25 ppm and 50 ppm, respectively. As a positive control, arbutin was also treated at 25 ppm, 50 ppm, 100 ppm and 200 ppm. Tyrosinase activity was assessed by measuring the absorbance at 490 nm using a microplate reader (Bio-Rad 3550, Richmond, Calif., U.S.A.) after an enzyme reaction for 20 minutes at 37° C.

The inhibitory effect of tyrosinase activity ($IC_{50}$) by the seven types of ginsenosides (GS #01-GS #06, GS #10) isolated from the *ginseng* seed extract was calculated, and the results are shown in Table 3.

TABLE 3

| Test materials | Control | GS#01 | GS#02 | GS#03 | GS#04 | GS#05 | GS#06 | GS#10 | Arbutin |
|---|---|---|---|---|---|---|---|---|---|
| $IC_{50}$ (ppm) | — | 23 | 30 | 27 | 31 | 47 | 53 | 15 | 149 |

As shown in the above table, all ginsenosides isolated from the *ginseng* seed extract were outstanding in the tyrosinase activity inhibitory effect as compared to arbutin, a positive control. In particular, it was confirmed that the novel ginsenoside compound 10 (GS #10) of the present disclosure has the most excellent activity inhibition of tyrosinase as compared to the previously known ginsenoside compounds 1-6 (GS #01-GS #06), which are comparative examples of the present disclosure, and thus has the excellent brightening efficacy. This is due to the chemical structural difference, which means that the novel ginsenoside PG-RT$_8$ of the present disclosure is far superior in skin brightening effect among *ginseng* seed-derived ginsenosides, and shows a strong skin brightening efficacy as compared to previously known steroidal saponins.

[Test Example 2] Comparison of Skin Brightening Efficacy 2

In order to compare the skin brightening effect of ginsenosides isolated from the *ginseng* seed extract, the effect of melanin production inhibition was evaluated as follows.

Specifically, the degree of intracellular melanin production was measured by Dooley's method. The cell line was a Mel-Ab cell line (Falcon, U.S.A.) derived from the skin pigment of C57BL/6. The culture was performed under the condition of 37° C., 5% $CO_2$ in a DMEM medium containing 10% of fetal placental serum, 100 nM of 12-O-tetradecanoylphorbol-13-acetate, 1 nM of Cholera Toxin. The cultured Mel-Ab cells were detached with 0.25% of trypsin-EDTA, inoculated again in the same number (1×10$^5$ cells/well) in a 24-well plate, and then treated with the test materials for two consecutive days from the second day by means of replacing with a medium containing the test materials. As the test material, the novel ginsenoside GS #10 of an embodiment of the present disclosure and ginsenosides GS #01-GS #06, which are comparative examples of the present disclosure were treated at 5 ppm, 10 ppm, 25 ppm and 50 ppm, respectively. As a positive control, kojic acid was treated at 25 ppm, 50 ppm and 100 ppm, and DMSO (dimethyl sulfoxide) was used as a control. After 5 days, 1N—NaOH was treated to dissolve melanin contained in the cells, and the amount of melanin was measured by measuring the absorbance at 400 nm. The concentration of a material ($IC_{50}$) required to reduce melanin production in melanocytes by half was calculated. The results are shown in Table 4 below.

TABLE 4

| Test materials | Control | GS#01 | GS#02 | GS#03 | GS#04 | GS#05 | GS#06 | GS#10 | Kojic acid |
|---|---|---|---|---|---|---|---|---|---|
| $IC_{50}$ (ppm) | — | 37 | 35 | 39 | 38 | 57 | 54 | 22 | 39 |

As shown in the above table, it is shown that the novel ginsenoside compound 10 (GS #10) of the present disclosure effectively inhibits the production of melanin as compared to the previously known ginsenoside compounds 1-6 (GS #01-GS #06), which are comparative examples of the present disclosure. It was confirmed that it has a skin brightening effect superior to kojic acid, which is a positive control known to have an excellent skin brightening effect.

[Test Example 3] Cytotoxicity

The cell growth in the presence of novel ginsenoside GS #10, which is an example of the present disclosure, was evaluated using Cell Counting Kit (CCK)-8, in order to exclude the possibility that ginsenosides may affect skin brightening efficacy through cytotoxic activity.

Specifically, the viability of SH-SY5Y cells was assessed using CCK-8 assay according to manufacturer's instructions (Dojindo, Md., USA). CCK-8, a cell viability detection reagent, was added to the cultured SH-SY5Y cells and incubated for 2 hours in a wet atmosphere. Then, absorbance was measured at 450 nm, and the cell viability was marked as a percentage (%) of the absolute optical density of each sample relative to the untreated sample. At this time, the concentration of the novel ginsenoside GS #10, which is an example of the present disclosure, contained in the medium in which the cells were cultured was 0.1, 1, 5, 10, 20, and 50 μM, respectively.

Figure 11:
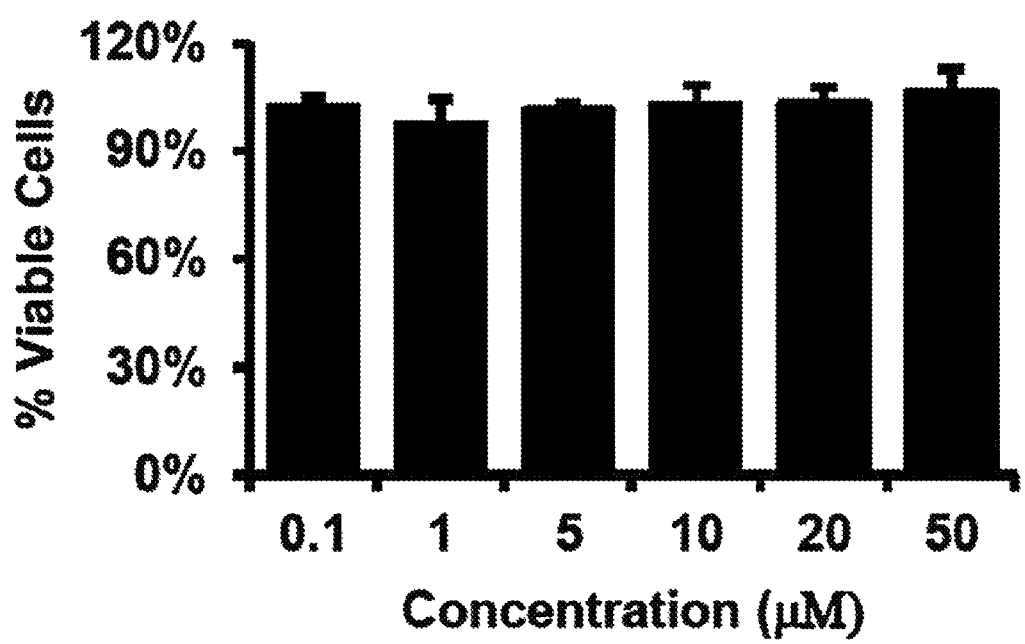
FIG. 11 is a diagram illustrating the cell viability (% Viable cells) of compound 10 (GS #10) corresponding to the novel ginsenoside of the present disclosure. (* $P<0.001$ vs. (−),  $P<0.01$ vs (−), * $P<0.05$ vs. (−))

As a result, as shown in FIG. 11, the novel ginsenoside GS #10, which is an example of the present disclosure, did not exhibit cytotoxicity up to 50 μM. This indicates that the novel ginsenoside, which is an example of the present disclosure, may exhibit a skin brightening effect without adversely affecting cell viability.

This suggests that the novel ginsenoside PG-RT$_8$ of an embodiment of the present disclosure has various strong skin brightening properties and has a pharmaceutical potential as a skin brightening agent.

[Test Example 4] Skin Accumulated Irritation Experiment

Human repeated insult patch tests (HRIPT) were performed to confirm whether the novel ginsenoside GS #10, which is an example of the present disclosure, has a skin accumulated irritation and to calculate a concentration range that can be used on the skin.

Specifically, 15 healthy adult subjects were randomly selected, and the test composition containing 0.5 wt %, 1 wt %, and 3 wt % of the compound (the skin composition comprising an emulsifier, a stabilizer, purified water, etc. in addition to the compound) was added dropwise by 20 μl per chamber (IQ chamber, Epitest Ltd, Finland). After 24 hours from patching the upper right part of the back of a subject, it was replaced with the new patch. In this way, the skin reactions were examined before and after each patch while performing nine patches three times a week for a total of three weeks. The skin reactions were confirmed up to 48 hours after removing the final patch, and the average reactivity was obtained. The results are shown in Table 5 below.

TABLE 5

| Test substance and content | Number of subjects with ±, +, or ++ reactivity (Unit: person) | | | | | | | | | |
|---|---|---|---|---|---|---|---|---|---|---|
| | Once | twice | Three times | Four times | Five times | Six times | Seven times | Eight times | Nine times | Average reactivity |
| Control | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| 0.5 wt % of GS#10 | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| 1 wt % of GS#10 | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |
| 3 wt % of GS#10 | 0 | 0 | 0 | 0 | 0 | 0 | 0 | 0 | 0 | 0 |
| | 0 | 0 | 0 | 0 | 0 | 0 | 0 | 0 | 0 | |
| | 0 | 0 | 0 | 0 | 0 | 0 | 0 | 0 | 0 | |

[[Reactivity]]–: Negative (no response) ±: Suspicious or slight erythema, or the like +: Weak reactions (without vesicles), erythema, papules ++: Severe reactions (with vesicles), erythema, papules, vesicles +++: Strong reaction, bulla reaction.
[[Average Reactivity Formula]]Average Reactivity = [{(Sum of the number of subjects with reactivity multiplied by reaction index)/(Total number of subjects × Maximum score (4 points))} × 100]/ Number of Tests (9 times).
In the above formula, if the reactivity is -, the reaction index is 0, if the reactivity is ±, the reaction index is 1, if the reactivity is +, the reaction index is 2, and if the reactivity is ++, the reaction index is 4.
It is determined as a safe composition when the average reactivity is less than 3.

The skin response was determined according to the criteria of the International Contact Dermatitis Research Group (ICDRG). As a result, as shown in the above table, the novel ginsenoside GS #10, which is an example of the present disclosure, showed (−) reactivity in all content range (there was no subjects with reactivity of ±, +, ++, or +++). This means that the novel ginsenoside GS #10, which is an example of the present disclosure, has no skin accumulated irritation and can be used safely on the skin.

Hereinafter, formulation examples of the composition according to one embodiment of the present specification will be explained. However, the formulation examples can be applied to various other formulations and are not intended to limit the present specification but only to specifically explain the present disclosure.

[Formulation Example 1] Softening Tonic (Skin Lotion)

The softening tonic was prepared in a conventional method according to the composition shown in the table below.

TABLE 6

| Compounding components | Contents (wt %) |
|---|---|
| PG-RT$_8$ | 0.1 |
| Glycerin | 3.0 |
| Butylene glycol | 2.0 |
| Propylene glycol | 2.0 |
| Carboxy vinyl polymer | 0.1 |
| PEG-12 nonylphenyl ether | 0.2 |
| Polysorbate 80 | 0.4 |
| Ethanol | 10.0 |
| Triethanolamine | 0.1 |
| Preservative, pigment, perfume | Proper amount |
| Purified water | Balance |

[Formulation Example 2] Nourishing Tonic (Milk Lotion)

The nourishing tonic was prepared in a conventional method according to the composition shown in the table below.

TABLE 7

| Compounding components | Contents (wt %) |
|---|---|
| PG-RT$_8$ | 0.1 |
| Glycerin | 3.0 |
| Butylene glycol | 3.0 |
| Propylene glycol | 3.0 |
| Carboxy vinyl polymer | 0.1 |
| Bees wax | 4.0 |
| Polysorbate 60 | 1.5 |
| Caprylic/Capric triglycerides | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Preservative, pigment, perfume | Proper amount |
| Purified water | Balance |

[Formulation Example 3] Massage Cream

The massage cream was prepared in a conventional method according to the composition shown in the table below.

TABLE 8

| Compounding components | Contents (wt %) |
|---|---|
| PG-RT$_8$ | 0.1 |
| Glycerin | 8.0 |
| Butylene glycol | 4.0 |
| Liquid paraffin | 45.0 |
| β-glucan | 7.0 |
| Carbomer | 0.1 |
| Caprylic/Capric triglycerides | 3.0 |
| Bees wax | 4.0 |
| Cetearyl glucoside | 1.5 |
| Sorbitan Sesquioleate | 0.9 |
| Vaseline | 3.0 |
| Paraffin | 1.5 |
| Preservative, pigment, perfume | Proper amount |
| Purified water | Balance |

[Formulation Example 4] Tablet 100 mg of ginsenoside PG-RT$_8$, 400 mg of lactose, 400 mg of corn starch, and 2 mg of magnesium stearate were mixed, and then tableted to prepare a tablet in accordance with a conventional method for preparing tablets.

[Formulation Example 5] Capsule 100 mg of ginsenoside PG-RT$_8$, 400 mg of lactose, 400 mg of corn starch, and 2 mg of magnesium stearate were mixed, and then filled into gelatin capsules to prepare a capsule in accordance with a conventional method for preparing capsules.

[Formulation Example 6] Granule 50 mg of ginsenoside PG-RT$_8$, 250 mg of anhydrous glucose and 550 mg of starch were mixed, molded into granules using a fluidized bed granulator, and then filled into a pouch.

[Formulation Example 7] Drink 50 mg of ginsenoside PG-RT$_8$, 10 g of glucose, 0.6 g of citric acid, and 25 g of liquid oligosaccharides were mixed, added with 300 ml of purified water, and 200 ml of the mixture was filled in a bottle. After the bottle was filled, the content was sterilized at 130° C. for 4-5 seconds to prepare a drink.

[Formulation Example 8] Caramel formulation 50 mg of ginsenoside PG-RT$_8$, 1.8 g of corn syrup, 0.5 g of skim milk, 0.5 g of soy lecithin, 0.6 g of butter, 0.4 g of vegetable hardened oil, 1.4 g of sugar, 0.58 g of margarine, and 20 mg of table salt were mixed to prepare caramel.

[Formulation Example 9] Health Food

TABLE 9

| Components | Contents |
|---|---|
| PG-RT$_8$ | 100 mg |
| Vitamin mixture | |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

Although the composition ratio of the vitamin and inorganic mixture was obtained by a mixed composition using the components that are relatively suitable for health foods, it is irrelevant to arbitrarily modify the compounding ratio for carrying out the present disclosure. The above ingredients may be mixed according to the conventional method for preparing health foods, and then may be used for preparing a granule and preparing a health food composition according to the conventional method.

[Formulation Example 10] Healthy Drink

TABLE 10

| Components | Contents |
|---|---|
| PG-RT$_8$ | 10 mg |
| Citric acid | 1000 mg |
| Oligosaccharide | 100 g |
| Plum concentrate | 2 g |
| Taurine | 1 g |
| Purified water | Balance |
| Total volume | 900 ㎖ |

As shown in the table above, a balance of purified water was added to make a total volume of 900 ml, and the above components were mixed according to the conventional method for preparing a healthy drink, stirred and heated at 85° C. for about 1 hour, and then the resulting solution was filtered, obtained in a sterilized 2-liter container, sterilized sealed, and then refrigerated to prepare a healthy beverage composition.

[Formulation Example 11] Injection

Injections were prepared by conventional methods according to the compositions described in the table below.

TABLE 11

| Compounding components | Contents (wt %) |
|---|---|
| PG-RT$_8$ | 10-50 mg |
| Sterile distilled water for injection | Proper amount |
| pH regulator | Proper amount |

The present disclosure may provide the following embodiments as an example.

In a first embodiment, there may be provided a method for skin brightening comprising administering to a subject in need thereof an effective amount of (20S,24R)-6-O-r-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

In a second embodiment, in accordance with the first embodiment, there may be provided a method, wherein the (20S,24R)-6-O-β-D-glucopyranosyl(1→2)-β-D-glucopyranoside-dammar-3-one-20,24-epoxy-6a,12b,25-triol has the structure of following formula 1.

[Formula 1]

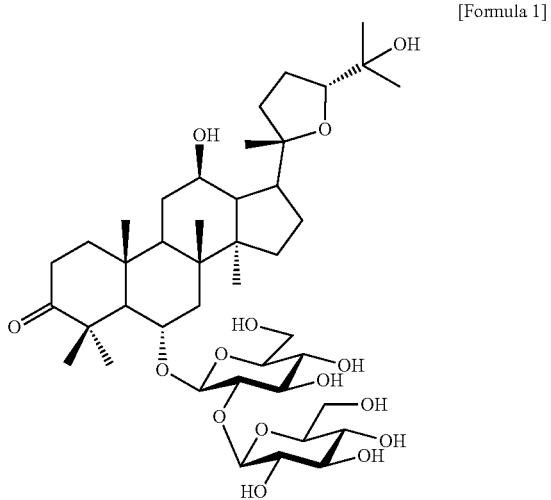

In a third embodiment, in accordance with the first or second embodiment, there may be provided a method, wherein the (20S,24R)-6-O-β-D-glucopyranosyl(1→2)-β-D-glucopyranoside-dammar-3-one-20,24-epoxy-6a,12b,25-triol is extracted from *ginseng* seed.

In a fourth embodiment, in accordance with any one or more of the first to third embodiments, there may be provided a method, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof inhibits the production of melanin.

In a fifth embodiment, in accordance with any one or more of the first to fourth embodiments, there may be provided a method, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof inhibits tyrosinase activity.

In a sixth embodiment, in accordance with any one or more of the first to fifth embodiments, there may be provided a method, wherein the dosage of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof is 0.05 mg/kg/day to 10 g/kg/day.

In a seventh embodiment, in accordance with any one or more of the first to sixth embodiments, there may be provided a method, wherein the method comprises a transdermal administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

In a eighth embodiment, in accordance with any one or more of the first to seventh embodiments, there may be provided a method, wherein the method comprises an oral or parenteral administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

In one aspect, the present disclosure may provide a composition comprising a novel ginsenoside, a pharmaceutically acceptable salt thereof, a hydrate or solvate thereof having an excellent effect on skin brightening. The novel ginsenosides exhibit remarkably excellent skin brightening efficacy as compared to the ginsenosides previously known to have a brightening effect.

The above embodiments have been disclosed for the purposes of illustration, and the description is not intended to limit the scope of the present disclosure. Accordingly, various modifications, variations, and substitutions may occur to those skilled in the art without departing from the spirit and scope of the present disclosure.

What is claimed is:

1. A method for skin brightening comprising administering to a subject in need thereof an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

2. The method of claim 1, wherein the (20S,24R)-6-O-β-D-glucopyranosyl(1→2)-β-D-glucopyranoside-dammar-3-one-20,24-epoxy-6a,12b,25-triol has the structure of following formula 1:

[Formula 1]

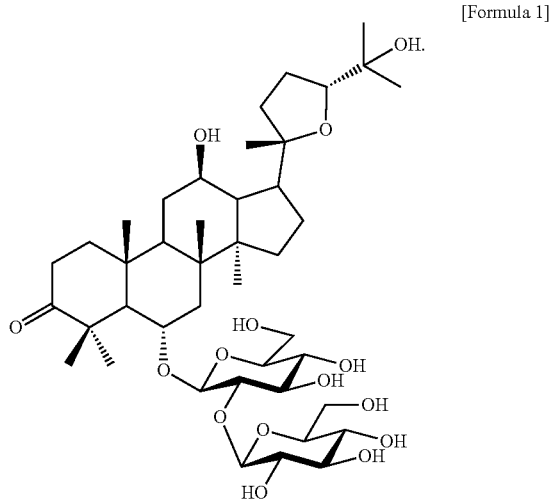

3. The method of claim 1, wherein the (20S,24R)-6-O-β-D-glucopyranosyl(1→2)-β-D-glucopyranoside-dammar-3-one-20,24-epoxy-6a,12b,25-triol is extracted from *ginseng* seed.

4. A method of inhibiting the production of melanin to a subject in need thereof comprising the step of administering an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

5. A method of inhibiting tyrosinase activity in a subject in need thereof comprising the step of administering an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

6. The method of claim 1, wherein the dosage of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof is 0.5 mg/kg/day to 10 g/kg/day.

7. The method of claim 1, wherein the method comprises transdermal administration of the (20 S,24R)-6-O-β-D-glucopyranosyl(1→2)-β-D-glucopyranoside-dammar-3-one- 20,24-epoxy-6a,12b,25-triol, a pharmaceutically acceptable salt thereof, a hydrate or a solvate thereof.

8. The method of claim 1, wherein the method comprises oral or parenteral administration of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate or a solvate thereof.

* * * * *